United States Patent [19]
Dumont

[11] Patent Number: 6,004,315
[45] Date of Patent: Dec. 21, 1999

[54] OPTICAL FIBER DIFFUSER AND METHOD OF MAKING

[75] Inventor: Michael G. Dumont, Hampton, N.H.

[73] Assignee: Focal, Inc., Lexington, Mass.

[21] Appl. No.: 08/714,189

[22] Filed: Sep. 16, 1996

[51] Int. Cl.⁶ .................................................. A61B 17/36
[52] U.S. Cl. .................................. 606/15; 606/16; 606/7; 607/93; 385/34; 385/123; 362/32; 65/385
[58] Field of Search ................................ 385/34, 77, 123, 385/127, 147, 901, 902; 362/32; 606/2, 10, 13, 15–17; 607/88, 89, 92, 93; 65/385, 397

[56] References Cited

U.S. PATENT DOCUMENTS

| | | |
|---|---|---|
| 4,248,214 | 2/1981 | Hannah et al. . |
| 4,336,809 | 6/1982 | Clark . |
| 4,544,235 | 10/1985 | Nishida et al. ............... 350/96.34 |
| 4,660,925 | 4/1987 | McCaughan, Jr. . |
| 4,693,556 | 9/1987 | McCaughan, Jr. . |
| 4,799,479 | 1/1989 | Spears . |
| 4,878,492 | 11/1989 | Sinofsky . |
| 4,995,691 | 2/1991 | Purcell, Jr. . |
| 5,019,075 | 5/1991 | Spears et al. . |
| 5,042,980 | 8/1991 | Baker et al. . |
| 5,154,708 | 10/1992 | Long et al. ............................ 606/16 |
| 5,190,538 | 3/1993 | Hussein et al. . |
| 5,196,005 | 3/1993 | Doiron et al. . |
| 5,209,748 | 5/1993 | Daikuzono . |
| 5,213,580 | 5/1993 | Slepian et al. . |
| 5,226,430 | 7/1993 | Spears et al. . |
| 5,248,311 | 9/1993 | Black et al. . |
| 5,269,777 | 12/1993 | Doiron et al. . |
| 5,292,320 | 3/1994 | Brown et al. . |
| 5,303,324 | 4/1994 | Lundahl . |
| 5,330,465 | 7/1994 | Doiron et al. . |
| 5,334,206 | 8/1994 | Daikuzono . |
| 5,380,318 | 1/1995 | Daikuzono . |
| 5,401,270 | 3/1995 | Muller et al. . |
| 5,410,016 | 4/1995 | Hubbell et al. . |
| 5,415,654 | 5/1995 | Daikuzono . |
| 5,536,235 | 7/1996 | Van Den Bergh et al. ............ 606/2 |
| 5,623,940 | 4/1997 | Daikuzono ........................... 606/15 |
| 5,728,092 | 3/1998 | Doiron et al. ........................ 606/15 |
| 5,754,717 | 5/1998 | Esch .................................... 606/16 |
| 5,772,657 | 6/1998 | Hmelar et al. ...................... 606/15 |
| 5,772,658 | 6/1998 | Konwitz .............................. 606/15 |
| 5,807,390 | 9/1998 | Fuller et al. ......................... 606/17 |

FOREIGN PATENT DOCUMENTS

| | | |
|---|---|---|
| 0588 078 A2 | 3/1994 | European Pat. Off. . |
| 0717 965 A1 | 6/1996 | European Pat. Off. . |
| 2154761 | 9/1985 | United Kingdom . |
| WO91 06251 | 5/1991 | WIPO . |
| WO91/06251 | 5/1991 | WIPO . |

OTHER PUBLICATIONS

H. Fujii et al, "Light Scattering Properties of a RoughEnded Optical Fiber", Optics & Laser Tech., Feb. 1984, pp. 40–44.

Primary Examiner—Linda C. M. Dvorak
Assistant Examiner—Bryan K. Yarnell
Attorney, Agent, or Firm—Wolf, Greenfield & Sacks, P.C.

[57] ABSTRACT

An optical fiber device includes a polymeric optical fiber having a proximal end for coupling to a source of light, and a diffusing region. The polymeric optical fiber includes a core and a cladding around the core. The diffusing region includes a length of the polymeric optical fiber in which the cladding is partially removed to expose the core and in which the exposed core and the remaining cladding have a roughened surface for outwardly diffusing light carried through the polymeric optical fiber. The diffusing region is preferably formed by abrasion, for example by directing a particle jet at the optical fiber while rotating and translating the optical fiber with respect to the particle jet. The particle jet may include microscopic glass beads which roughen the optical fiber core. The density of scattering sites may be varied along the length of the diffusing region to produce a desired light output pattern. The optical fiber device is useful in medical applications, including as a component of catheter or endoscopic systems.

46 Claims, 5 Drawing Sheets

OPTICAL FIBER DIFFUSER AND METHOD OF MAKING

FIELD OF THE INVENTION

This invention relates to optical fiber devices for transmission of radiation for medical applications and, more particularly, to an optical fiber diffuser integrally formed on a plastic optical fiber and to methods for making the optical fiber diffuser.

BACKGROUND OF THE INVENTION

Medical applications of light have been widely studied. When light is to be delivered to a site within a patient's body, such as a blood vessel or other body passage, an optical fiber is typically used for transmission of the light. Optical fibers have small diameters, are relatively flexible and can deliver reasonably high energy levels. An example of the application of light is laser balloon angioplasty, which involves the simultaneous application of laser energy and pressure to a plaque-narrowed region of an artery, as described in U.S. Pat. No. 4,799,479 issued Jan. 24, 1989 to Spears. Optical fiber devices usually have an element at the distal tip for controlling the output pattern of the light. Various optical fiber tip configurations have been described, including a lens for expanding or focusing the light, a heating element for converting the light energy to thermal energy and a diffusing tip for directing the light outwardly in a generally cylindrical pattern. Optical fiber devices may be used for a variety of applications, including but not limited to tissue vaporization, tissue coagulation, photoactivation of drugs and photopolymerization.

A diffusing tip is typically used when a generally uniform light output pattern is required over a prescribed length of a body passage. Several prior art techniques have been disclosed for directing light outwardly from the diffusing tip of an optical fiber. A tapered optical fiber tip surrounded with a diffusing medium for light radiation treatment of tumors is disclosed in UK Patent Application No. 2,154,761, published Sep. 11, 1985. A tapered optical fiber diffusing tip is also disclosed in U.S. Pat. No. 4,878,492 issued Nov. 7, 1989 to Sinofsky et al. An optical fiber surrounded with a scattering medium for producing a cylindrical pattern of light at the tip of an optical fiber is disclosed in U.S. Pat. No. 4,660,925 issued Apr. 28, 1987 to McCaughan, Jr. A technique for roughening the surface of an optical fiber tip to cause wide angle radiation of light is disclosed by H. Fujii et al. in "Light Scattering Properties of a Rough-Ended Optical Fiber," *Optics and Laser Technology,* February 1984, pages 40–44.

Optical fiber devices for medical applications have typically utilized glass or silica optical fibers. U.S. Pat. No. 4,995,691 issued Feb. 26, 1991 and U.S. Pat. No. 5,190,538 issued Mar. 2, 1993 suggest that polymeric optical fibers are suitable for medical applications.

The aforementioned U.S. Pat. No. 4,799,479 discloses a glass optical fiber that extends through a catheter and terminates in a light-disseminating tip located within an inflatable balloon. Spears teaches that the light-disseminating tip can be provided by removing the cladding from the fiber tip and roughening the fiber core surface. Optical fibers with roughened distal ends are also disclosed in U.S. Pat. No. 5,401,270 issued Mar. 28, 1995 to Muller et al. and PCT Publication No. WO91/06251, published May 16, 1991. An optical fiber diffusion tip wherein the cladding has a thickness selected to transmit a portion of the light radiation carried through the optical fiber is disclosed in U.S. Pat. No. 5,042,980 issued Aug. 27, 1991 to Baker et al. An optical fiber device wherein openings are formed in the cladding to expose the core without physical alteration of the core is disclosed in U.S. Pat. No. 5,248,311 issued Sep. 28, 1993 to Black et al.

All known prior art optical fiber diffusing tips have had one or more disadvantages. Diffusion tips wherein a glass optical fiber has a roughened core surface have a tendency to break, because the fiber is weakened in the roughened area. Glass is known to have high notch sensitivity, and thus a tendency to break at the site of a surface defect, because of the low energy of propagation of a crack. Plastics, even relatively brittle plastics such as polystyrene or polymethylmethacrylate, in contrast, have a much higher crack propagation energy, and are thus much tougher than glass. Breakage of a diffusion tip within a patient's body may have extremely serious adverse consequences. Other diffusion tips, such as those in which a scattering medium is enclosed in a transparent tube, have a larger diameter than the optical fiber and may not be usable in certain applications which require extremely small diameters. Many prior art diffusion tips involve fabrication techniques which are complex and expensive. Prior art diffusion tips have frequently exhibited non-uniform radiation patterns and/or radiation patterns which were not repeatable from unit to unit.

SUMMARY OF THE INVENTION

According to the present invention, an optical fiber device is provided. The optical fiber device comprises a polymeric optical fiber having a proximal end for coupling to a source of light and a diffusing region. The polymeric optical fiber comprises a core and a cladding around the core. The diffusing region comprises a length of the polymeric optical fiber in which the cladding is partially removed to expose the core and in which the exposed core and the remaining cladding have a roughened surface for outwardly diffusing radiation carried through the polymeric optical fiber. The diffusing region is preferably monolithic with the rest of the optical fiber device. "Monolithic" is used in the sense of being made of one piece of material, without any joints or bonds. Such a device is resistant to breaking while in use, which, as noted, can be life-threatening or fatal.

In a preferred embodiment, the core of the polymeric optical fiber comprises polymethylmethacrylate (PMMA) and the cladding comprises fluorine-doped PMMA. The diffusing region is typically located at the distal end of the optical fiber, but may be located intermediate the proximal end and the distal end.

The roughened surface of the core and the cladding may comprise a plurality of scattering sites. The density of scattering sites may be variable along the length of the diffusing region, and may be selected to provide a substantially uniform radiation pattern along the length of the diffusing region. The length of the diffusing region can be varied at will. In contrast to prior art diffusers, there is a much higher upper limit of the ratio of the length of the diffuser to the diameter of the fiber.

According to another aspect of the invention, a method for fabricating an optical fiber device is provided. The method comprises the steps of providing an elongated optical fiber, including a core and a cladding around the core, and treating a selected region of the fiber to partially remove the cladding and expose the core, and to roughen the surface of the exposed core and the remaining cladding, thereby forming a diffusing region having a plurality of scattering sites at which light may escape from the core and be diffusely scattered outwardly from the axis of the fiber. The density of the scattering sites is controlled during fabrication to provide the desired radiation pattern.

In a preferred embodiment, the fiber is treated by directing a particle jet at the optical fiber, rotating the optical fiber about its longitudinal axis with respect to the particle jet and translating the optical fiber along the longitudinal axis with respect to the particle jet. The particles in the particle jet preferably comprise glass beads having diameters in a range of about 2–10 micrometers.

The method may further comprise the step of varying the density of scattering sites as a function of axial position along the diffusing region. A variable density of scattering sites may be provided by translating the optical fiber at a variable rate or by directing the particle jet with a variable number of particles per unit time.

The method may further comprise the steps of directing light through the optical fiber and monitoring light output from the diffusing region as the diffusing region is being fabricated. The light output from the diffusing region may be used to control the fabrication process by controlling the particle jet, by controlling rotation of the optical fiber and/or by controlling translation of the optical fiber.

According to a further aspect of the invention, a catheter is provided. The catheter comprises an elongated flexible tube having a distal end and a proximal end, and an optical fiber device positioned within the flexible tube for carrying light through the flexible tube. The optical fiber device comprises a polymeric optical fiber including a proximal end for coupling to a source of light and a diffusing region positioned distally on the fiber. The polymeric optical fiber comprises a core and a cladding around the core. The diffusing region comprises a length of the polymeric optical fiber in which the cladding is partially removed to expose the core and in which the exposed core and the remaining cladding have a roughened surface for outwardly diffusing light carried through the polymeric optical fiber.

BRIEF DESCRIPTION OF THE DRAWINGS

For a better understanding of the present invention, reference is made to the accompanying drawings which are incorporated herein by reference and in which.

DETAILED DESCRIPTION

Figure 1:
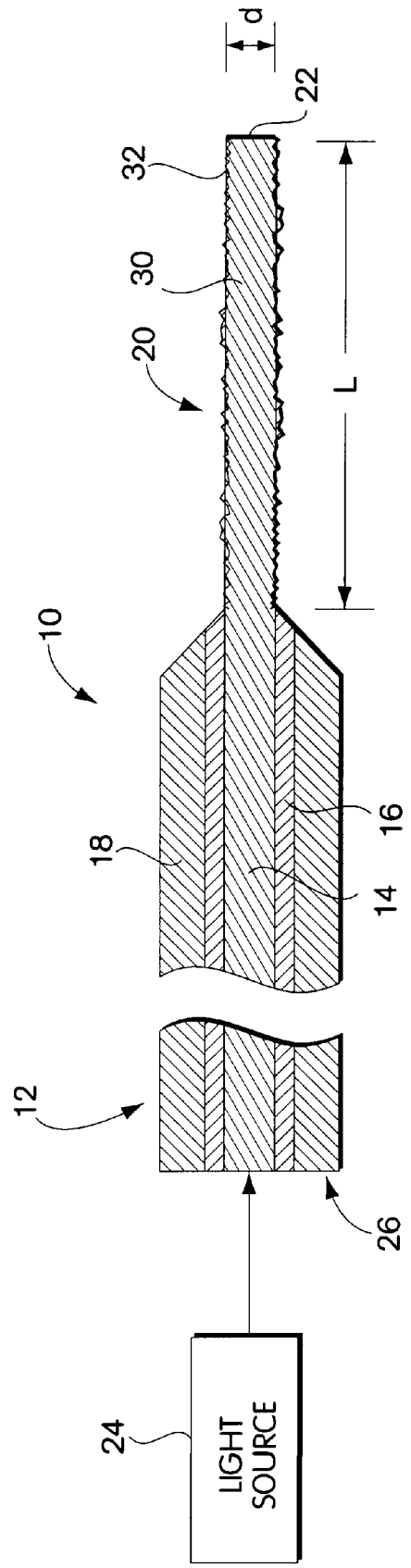
FIG. 1 is a schematic representation of an embodiment of an optical fiber device in accordance with the present invention.

An optical fiber device 10 in accordance with an embodiment of the present invention is shown in FIG. 1. The optical fiber device 10 is shown enlarged and not to scale for ease of understanding. The optical fiber device 10 includes an optical fiber 12 having a core 14, a cladding 16 and an optional outer protective jacket 18. The device further includes at least one diffusing region. The diffusing region may be formed as a diffusing tip 20 located in a region adjacent to a distal end 22 of the optical fiber device. As is conventional in optical fibers, the cladding 16 has an index of refraction that is lower than the index of refraction of core 14, and jacket 18, when present, has an index of refraction that is higher than the indices of refraction of both the core 14 and the cladding 16. (Such a jacket may also be opaque.) Light, such as energy from a light source 24, is coupled to a proximal end 26 of the optical fiber 12. Light incident on the interface between core 14 and cladding 16 at less than the critical angle is reflected back into the core 14 and is guided through the fiber to the diffusing tip 20. The diffusing tip 20 directs the light outwardly (laterally with respect to the longitudinal axis of the optical fiber) in a cylindrical or other desired radiation pattern, as described below. A lens system (not shown) may be utilized for focusing light from source 24 onto the proximal end 26 of optical fiber 12, as is known in the art.

The optical fiber 12 is preferably a polymeric material, such as polymethylmethacrylate (PMMA). More specifically, the core 14 may be PMMA, and the cladding 16 may be fluorine-doped PMMA. Other suitable polymeric optical fiber materials include polycarbonate and fluoropolymers. In a preferred embodiment, the optical fiber core and cladding have an outside diameter of 260 micrometers. However, it will be understood that larger and smaller diameter optical fiber devices are included within the scope of the present invention. The polymeric, or plastic, optical fiber has the advantage over glass and silica optical fibers that a small diameter diffusing tip can be provided without substantial risk of breakage. The diameter d of the diffusing tip 20 does not exceed the diameter of the optical fiber 12 and usually has a smaller diameter than the optical fiber 12.

The diffusing tip 20 comprises an abraded section 30 which extends beyond optional jacket 18, if present, of optical fiber 12. The abraded section 30 is integral with core 14 and cladding 16 in the remainder of optical fiber 12 so as to form a continuous, single-piece core from the proximal end 26 to the distal end 22 of optical fiber device 10. Part of the cladding 16 is removed from the optical fiber 12 in the region of diffusing tip 20 by an abrasive process. In particular, the cladding is partially removed to expose one or more regions of the core, and the remaining cladding and the exposed core are roughened, or abraded, to form scattering sites. Scanning electron microscope evaluation of diffusing tips in accordance with the invention has confirmed that the cladding is removed in some regions of the diffusing tip, while in other regions the cladding remains. The remaining cladding and the exposed core are roughened. The abraded section 30 has a length L which corresponds to the length of a desired radiation pattern.

The abraded section 30 has a roughened surface 32 which causes light to be directed outwardly from the diffusing tip 20. The roughened surface 32 comprises multiple scattering sites, or surface irregularities, having dimensions on the order of a few micrometers. Fragments of the cladding 16 will normally be present on the roughened surface 32 and will participate in forming the light output pattern of the diffusing tip 20. A portion of the light passing through abraded section 30 and incident on the surface irregularities is directed outwardly from the diffusing tip 20 rather than being reflected back into the core material. Another portion of the light is reflected within the abraded section 30 and may be directed outwardly by surface irregularities further downstream in the direction of transmission. In this way, the light is gradually directed outwardly over the length L of the diffusing tip 20. The result is a light output pattern over the length L of diffusing tip 20. The light output pattern typically has a generally cylindrical configuration and is preferably substantially uniform along length L. However, other light output patterns may be utilized within the scope of the present invention. Preferably, most of the light is directed outwardly through roughened surface 32 so that little or no energy passes through the distal end 22 of optical fiber 12. However, the invention is intended to include embodiments where a portion of the energy passes through distal end 22.

The diffusing tip 20 typically emits light over the full 360 degrees of the abraded section 30. However in some cases, a light output pattern of less than 360 degrees may be required. A light output pattern of less than 360 degrees may be obtained, for example, by coating a portion of the diffusing tip 20 with an opaque material, or by leaving a part of the diffusing tip 20 unabraded.

As noted above, there is no particular ratio of the parameters L and d which is required. However, prior art diffusers are believed to be generally limited in this ratio to values of 20 or less—for example, a length L of 2 millimeters on a 100-micrometer fiber—before requiring additional protection from the stresses of bending. Fiber diffusers of the invention can have L/d ratios of 50, 100, 200, 300 or more without encountering mechanical problems or becoming fragile.

As discussed above, light passing through abraded section 30 is gradually directed outwardly by the roughened surface 32, thereby gradually reducing the light remaining within section 30 as a function of distance along section 30. Thus, when roughened surface 32 has a uniform density of scattering sites along the length of section 30, the intensity of the light output pattern decreases as the distance from distal end 22 decreases. In order to counteract this effect and produce a uniform intensity along length L, the density of surface irregularities may be varied along length L of diffusing tip 20. In order to produce a substantially uniform intensity, the density of surface irregularities is increased as the distance from distal end 22 decreases. More generally, the density of surface irregularities may be varied as a function of distance along the length of diffusing tip 20 to produce a desired radiation pattern.

The diffusing tip 20 shown in FIG. 1 is located at the distal end of the optical fiber device 10. In alternate embodiments, the optical fiber device according to the invention may include one or more diffusing regions intermediate the proximal end and the distal end of the optical fiber device. An optical fiber device of this type may or may not have a diffusing region at its distal end. Each diffusing region may have any desired length. In each case, the diffusing region comprises a section of the optical fiber lacking a jacket, in which section the cladding is partially removed to expose the core and in which the exposed core and the remaining cladding have a roughened surface to direct light outwardly in a desired light output pattern.

The optical fiber device of the present invention can be used to transmit light of any wavelength within the transmission band of the optical fiber material. The light may be in the visible, infrared or ultraviolet wavelength ranges.

Figure 2:
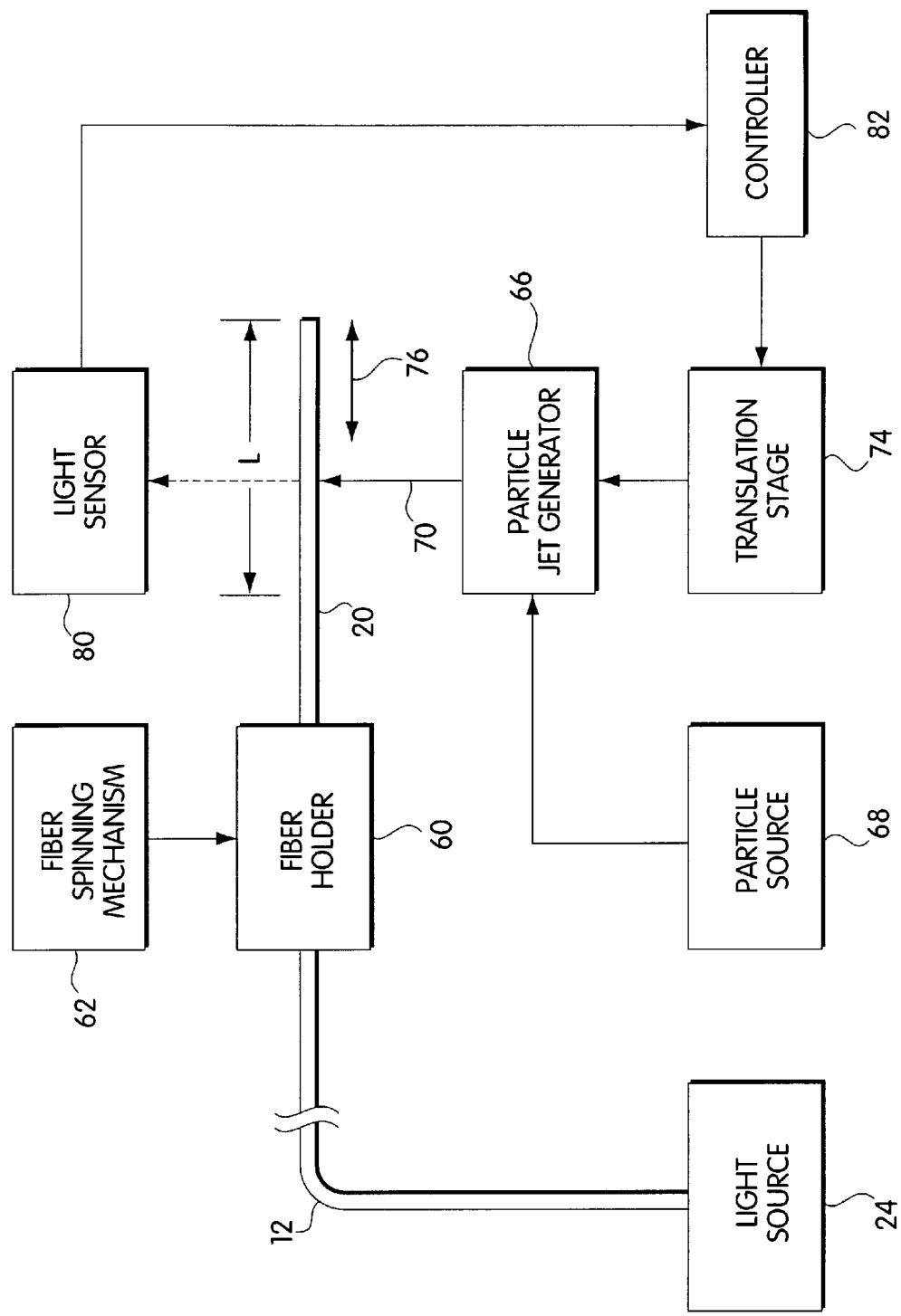
FIG. 2 is a block diagram of an example of a system for fabricating a diffusing tip in accordance with the present invention.

An example of a suitable system for fabricating an optical fiber device in accordance with the present invention is shown in FIG. 2. The system is used for forming diffusing tip 20 at the distal end of optical fiber 12. The jacket 18, if present, is removed from the optical fiber 12 in the region of diffusing tip 20 by chemical or mechanical stripping. The optical fiber 12 is placed in a fiber holder 60 with the region of diffusing tip 20 exposed for processing. The fiber holder 60 is mounted in a fiber spinning mechanism 62. The spinning mechanism 62 rotates the portion of the optical fiber where the diffusing tip is to be formed in alternating clockwise and counterclockwise directions about its longitudinal axis. The fiber is typically rotated by one or a few turns in each direction. The optical fiber 12 is mounted in fiber holder 60 with sufficient slack to prevent excessive stress on the fiber as it is being rotated.

A particle jet generator 66 directs a particle jet 70 at the optical fiber 12 in the region of diffusing tip 20. The particle jet 70 is a stream of fine particles selected to partially remove cladding 16 and to roughen exposed portions of core 14 and the remaining cladding 16. The particle jet generator 66 receives a supply of particles from a particle source 68. The particles may, for example, be glass beads having diameters in the range of about 2–10 micrometers. The glass beads produce surface irregularities on the core 14 and cladding 16 which act as scattering sites. Glass beads in the above diameter range typically produce surface irregularities having dimensions on the order of about 5 micrometers, which have been found to produce effective scattering of visible light from a PMMA core.

Other abrasives may be used, such as particles of alumina, or of silicon carbide, or other particulate abrasives known in the art. In general, the particle composition and size are selected based on the size of the fiber and the material of the optical fiber core and cladding. Typically, and for use with visible light, the particle size will be selected to give scattering sites with dimensions on the order of about 1 to 50 micrometers, preferably 2 to 20 micrometers, still more preferably 3 to 10 micrometers, and most preferably about 5 micrometers. Larger sizes would be more acceptable with longer wavelength light, such as infrared. Moreover, the typical size of the scattering sites should be substantially smaller than the diameter of the fiber, to provide uniformity.

The particle jet generator 66 may, for example, be a miniature sandblasting device, such as a Hunter Products, Inc. Microjet, Model 200. It is operated at an air pressure of 2040 psi, preferably about 35 psi. The nozzle diameter may be 0.020 inches or 0.010 inches. The nozzle to fiber distance may be 0.5 to 2.0 inches.

The particle jet generator 66 may be mounted on a linear translation stage 74 which translates the particle jet 70 in a direction indicated by arrow 76 along the length of the diffusing tip 20. The translation stage 74 may, for example, be a Newport Research Corp. Model 430. The particle jet 70 is translated along the entire length of diffusing tip 20 to partially remove the cladding and expose the core, and to roughen the remaining cladding and the exposed core. In an alternate embodiment, the particle jet generator 66 can be stationary, and the diffusing tip 20 can be translated with respect to the particle jet 70. In operation, the fiber spinning mechanism 62 rotates diffusing tip 20 and linear translation stage 74 translates particle jet generator 76 as particle jet 70 is directed at the diffusing tip 20, thereby roughening the surface of the cladding and the exposed core in the region of diffusing tip 20.

While a miniature sandblaster is currently preferred, other means may be used for partially removing the cladding and roughening the remaining cladding and the exposed core to obtain the monolithic diffusing tips of the invention. For example, the fiber, with jacket, if any, removed, can be placed between layers of optical lapping paper and rolled back and forth between these laps by rolling on a surface, such as a laboratory bench. It is also possible, especially for larger fibers, to use a device employing sandpaper, such as an Eraser motorized wire stripper. Chemical etchants may also be used, provided that they are selected, according to the particular plastics of the fiber core and cladding, to produce a roughened, non-polished surface. Alternatively, ultrasonic agitation of the fiber in a bath of abrasive slurry may be effective. In either of these methods, the gradient may be produced by gradual withdrawal of the diffusing region from a bath. Centerless grinding may also be used.

As indicated above, the light output pattern produced by the diffusing tip 20 is a function of the distribution of surface irregularities on the optical fiber core. A greater number of surface irregularities per unit area increases light output for a given light input. The variation in surface irregularities over the length of diffusing tip 20 determines the light output pattern. In typical applications, a substantially uniform cylindrical light pattern is desired. However, other light patterns may be required for particular applications. Referring again to FIG. 2, an optional sensing system may be used to sense the light output from the diffusing tip 20 during fabrication and to control the fabrication parameters in real time. Light from source 24 is coupled to the proximal end of optical fiber 12, and a light sensor 80, such as a CCD detector, is positioned adjacent to diffusing tip 20. The light sensor 80 monitors the light output of the diffusing tip 20 during the fabrication process and provides a signal representative of the light output to a computerized controller 82. The computerized controller 82 is programmed to compare the light sensor signal with a value or range of values representative of a desired light output pattern and to control the fabrication process accordingly. For example, the speed of the linear translation stage 74 may be increased or decreased as necessary when the light sensor signal is outside a specified range. Other fabrication parameters may be controlled individually or in combination. For example, the number of particles per unit time in the particle jet 70 and/or the particle jet velocity may be controlled. In addition, the rate of rotation of the diffusing tip 20 may be controlled to produce a desired light output pattern.

The light sensor 80 provides real time sensing and control of the light output pattern. In other embodiments of the invention, the process parameters necessary to produce a desired light output pattern are determined experimentally, and the predetermined parameters are programmed in the controller 82. During fabrication of diffusing tip 20 the process is controlled in accordance with the predetermined parameters, which may include translation velocity as a function of time, particle jet parameters, fiber rotation parameters and combinations of these parameters.

As noted above, a substantially uniform cylindrical light output pattern is frequently desired. It has been found that a substantially uniform light output pattern is produced when the density of scattering sites along the length of diffusing tip 20 varies exponentially with distance.

Figure 3:
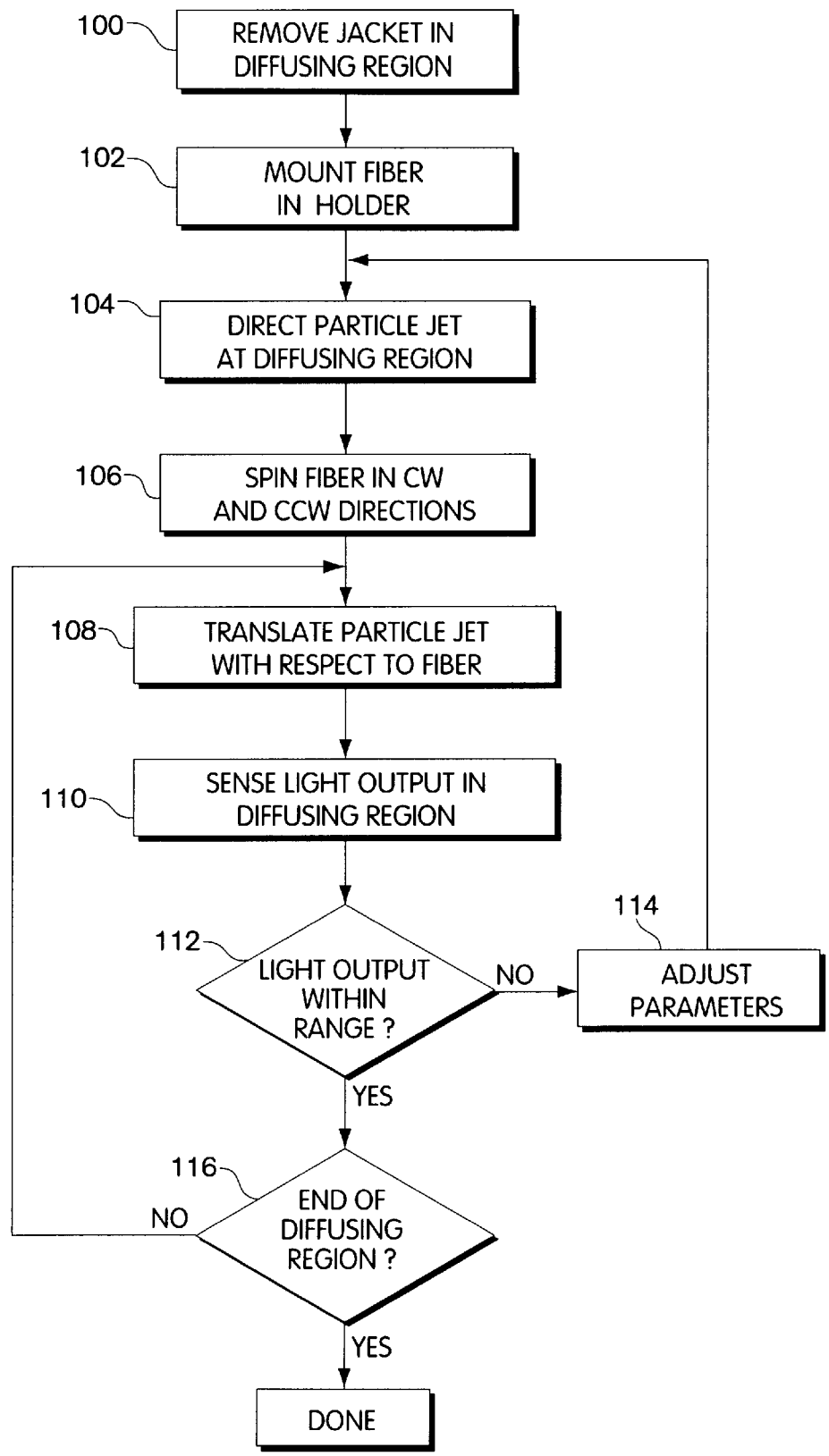
FIG. 3 is a flow chart that illustrates an embodiment of a process for fabricating a diffusing tip in accordance with the present invention.

A process implemented by the system of FIG. 2 is shown in FIG. 3. The jacket 18, if present, of optical fiber 12 is removed in the diffusing region 20 in step 100, and the fiber is mounted in holder 60 in step 102. Particle jet 70 is directed at the diffusing tip 20 in step 104 to partially remove cladding 16 and to roughen the remaining cladding and the exposed core 14. Simultaneously with step 104, the fiber is rotated in alternating clockwise and counterclockwise directions in step 106 and is translated relative to the particle jet 70 in step 108. When the light sensor 80 is utilized, the light output of the diffusing tip is sensed in step 110. When the light output is within a specified range as determined in step 112, the abrasion process continues until the end of the diffusing region is reached. When the sensed light output is outside the specified range, one or more of the fabrication parameters are adjusted in step 114. The process may utilize one or more passes along the length of the diffusing region. When light sensing and feedback control of process parameters are utilized, more than one pass may be used to permit parameter adjustment. In step 116, the process determines whether the end of the diffusing region has been reached. When the end of the diffusing region is reached, the process is complete. Otherwise, the process continues until the end of the diffusing region is reached. The light output is sensed during the fabrication process and the fabrication parameters are adjusted as necessary to obtain the desired light output pattern. By changing the specified range with which the light sensor signal is compared in step 112, the light output pattern can be changed.

Figure 5:
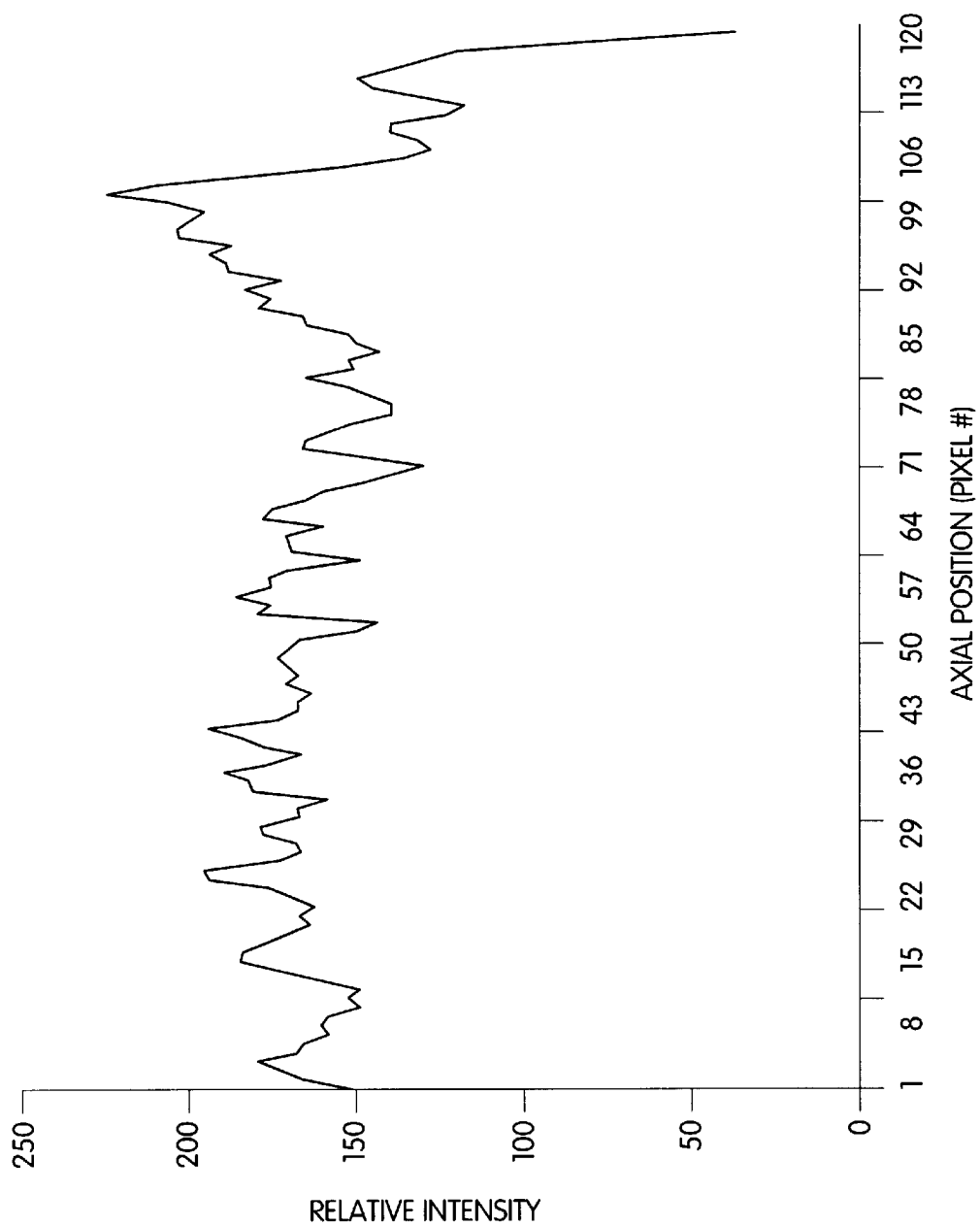
FIG. 5 is a graph of emitted intensity as a function of axial position for a diffusing tip in accordance with the invention.

One of the critical optical properties that can be controlled and customized or tailored to a particular application using this invention is the emitted intensity as a function of distance, or axial distribution, along the diffusing portion of the fiber. The resultant emitted intensity as a function of axial position for a typical optical fiber diffuser manufactured using the preferred technique is shown in FIG. 5. The emitted intensity, or axial distribution, shown was achieved using a 200 μm diameter, polymethylmethacrylate (PMMA), optical fiber. Emission length was 4.0 cm. The axial distribution was measured by imaging the emitting portion of the optical fiber onto a 8 mm×8 mm CCD camera (Cohu model 4812) using a close-up lens (Computar model Zoom 18-10812.5). The output of the CCD camera was input to a beam analyzer (Spiricon model LBA-100A). The intensity distribution of the image was analyzed using image analysis software (Spiricon LBA-3DA).

Figure 4:
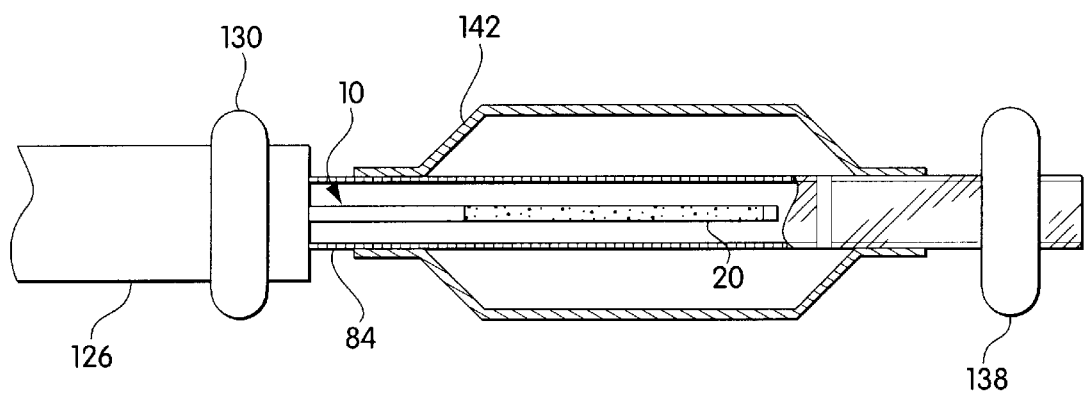
FIG. 4 is a cross-sectional view of the distal end of a catheter in accordance with an embodiment of the invention.

A simplified cross-sectional view of the distal end of a catheter utilizing an optical fiber device in accordance with the present invention is shown in FIG. 4. An outer catheter 126 bears a proximal occlusion balloon 130, while an inner catheter shaft 134 bears a distal occlusion balloon 138 and an angioplasty-type balloon 142. The inner shaft and the angioplasty-type balloon are made of transparent or translucent materials, such as polypropylene, or polyethylene terephthalate. The center of shaft 134 is hollow, and initially contains a guidewire. After guiding the catheter to the appropriate location over the guidewire, the guidewire is removed, and an optical fiber device of the invention is inserted through the hollow shaft. The distal end of the optical fiber device 10, including diffusing tip 20, is illustrated. Such a catheter, not necessarily having all of the balloons illustrated, can be used to direct light to a site for polymerizing a coating, as described in U.S. Pat. No. 5,410,016; or to use light to soften a paving material, as described in U.S. Pat. No. 5,213,580. Other uses could include illuminating a region treated with a drug used in phototherapy; ablating tissue or other material from a region, using high intensity or laser light; or simply illuminating a region uniformly for good visibility, as with an endoscope.

Furthermore, fabrication of a monolithic diffusing emission region on an optical fiber can be combined with other techniques. For example, it would be possible to dye the emission region of such an optical fiber with a fluorescent dye, such as a dye that can be used to sense the oxygen concentration, pH or other parameter of the blood. Then the exciting wavelength of light will be efficiently emitted in a particular region of the fiber, in the same place as the fluorescent probe is located, thereby diminishing background while enhancing the effective aperture of the fiber for transmitting the fluorescent emission back to a detector at the proximal end of the apparatus.

The preferred use for the diffuser of the invention is as part of a catheter system for treatment of blood vessels, especially the vessels of the heart. However, while the discussion and figures are couched in terms of use of the diffuser of the invention in a catheter suitable for such uses, the optical fiber of the invention is potentially of use in any medical application requiring the radial or substantially symmetric delivery of light to a region of the human body, particularly in circumstances where breaking of the diffuser while in use could be hazardous. Thus, the fiber could be used in an endoscopic or other surgical device in inspection or treatment in any hollow cavity of the body, particularly when reached through minimally invasive means such as a cannula, for example the cannula of a trocar. An example of such use would be inspection or treatment of the intestines, through a sigmoidoscope, colonoscope or similar device.

While there have been shown and described what are at present considered the preferred embodiments of the present invention, it will be obvious to those skilled in the art that various changes and modifications may be made therein without departing from the scope of the invention as defined by the appended claims.

What is claimed is:

1. An optical fiber device comprising a polymeric optical fiber including a proximal end for coupling to a source of light and a diffusing region, said polymeric optical fiber comprising a core and a cladding around said core, said diffusing region comprising a length of said polymeric optical fiber in which said cladding is partially removed to expose said core and in which the exposed core and the remaining cladding have a roughened surface for outwardly diffusing light carried through said polymeric optical fiber.

2. An optical fiber device as defined in claim 1 wherein the device is monolithic.

3. An optical fiber device as defined in claim 1 wherein said diffusing region is located at a distal end of said polymeric optical fiber.

4. An optical fiber device as defined in claim 1 wherein said diffusing region is located intermediate said proximal end and a distal end of said polymeric optical fiber.

5. An optical fiber device as defined in claim 1 wherein said core comprises polymethylmethacrylate (PMMA) and said cladding comprises fluorine doped PMMA.

6. An optical fiber device as defined in claim 1 wherein said roughened surface comprises a plurality of scattering sites and wherein a density of said scattering sites is variable along the length of said diffusing region.

7. An optical fiber device as defined in claim 6 wherein the density of said scattering sites increases with distance from the proximal end of said polymeric optical fiber.

8. An optical fiber device as defined in claim 6 wherein the density of said scattering sites along the length of said diffusing region is selected to provide substantially uniform intensity of light along the length of said diffusing region.

9. An optical fiber device as defined in claim 1 wherein the diameter of said diffusing region does not exceed the diameter of said polymeric optical fiber.

10. An optical fiber device as defined in claim 6 wherein said scattering sites have dimensions on the order of about 1 to 50 micrometers.

11. An optical fiber device as defined in claim 6 wherein said scattering sites have dimensions on the order of about 2 to 20 micrometers.

12. An optical fiber device as defined in claim 6 wherein said scattering sites have dimensions on the order of about 3 to 10 micrometers.

13. An optical fiber device as defined in claim 6 wherein said scattering sites have dimensions on the order of about 5 micrometers.

14. An optical fiber device as defined in claim 1 wherein said cladding is at least partially removed from said core in said diffusing region.

15. An optical fiber device as defined in claim 1 wherein said cladding is at least partially retained in said diffusing region.

16. An optical fiber device as defined in claim 1 wherein said optical fiber comprises a polymer selected from the group consisting of polymethylmethacrylate, polycarbonate and fluoropolymers.

17. An optical fiber device as defined in claim 1 wherein said diffusing region has a length and a diameter and wherein the ratio of the length of the diffusing region to the diameter of the diffusing region is greater than 50.

18. An optical fiber device as defined in claim 1 wherein said diffusing region has a length and a diameter and wherein the ratio of the length of the diffusing region to the diameter of the diffusing region is greater than 100.

19. An optical fiber device as defined in claim 1 wherein said diffusing region has a length and a diameter and wherein the ratio of the length of the diffusing region to the diameter of the diffusing region is greater than 200.

20. An optical fiber device as defined in claim 1 wherein said diffusing region has a length and a diameter and wherein the ratio of the length of the diffusing region to the diameter of the diffusing region is greater than 300.

21. A method for fabricating an optical fiber device, comprising the steps of:
    a) providing an elongated optical fiber including a core and a cladding around the core, said optical fiber having a longitudinal axis; and
    b) treating a selected region of said fiber to partially remove said cladding and expose said core, and to roughen a surface of the exposed core and the remaining cladding so as to form a diffusing region of said optical fiber.

22. A method as defined in claim 21 wherein the step of treating a selected region of said fiber includes:
    directing a particle jet at the optical fiber;
    rotating said optical fiber about said longitudinal axis with respect to said particle jet; and
    translating said optical fiber along said longitudinal axis with respect to said particle jet.

23. A method for fabricating an optical fiber device as defined in claim 21 further including the steps of:
    evaluating the light output pattern of the fiber; and
    continuing the step of treating a selected region of said fiber until the light output pattern of the fiber corresponds to a desired pattern.

24. A method as defined in claim 22 wherein the step of directing said particle jet includes directing glass beads.

25. A method as defined in claim 22 wherein the step of directing said particle jet includes directing glass beads having diameters in a range of about 2–10 micrometers.

26. A method as defined in claim 22 wherein the step of rotating said optical fiber includes alternately rotating said optical fiber in clockwise and counterclockwise directions.

27. A method as defined in claim 22 wherein the roughened surface of said core comprises a plurality of scattering sites on said core, said method further comprising the step of varying the density of said scattering sites as a function of longitudinal position along said diffusing region.

28. A method as defined in claim 27 wherein the step of varying the density of said scattering sites comprises performing the step of translating said optical fiber at a variable rate.

29. A method as defined in claim 27 wherein the step of varying the density of said scattering sites comprises performing the step of directing said particle jet with a variable number of particles per unit time.

30. A method as defined in claim 21 wherein the step of treating a selected region of said fiber comprises forming said diffusing region at a distal end of said optical fiber.

31. A method as defined in claim 21 wherein the step of treating a selected region of said fiber comprises forming said diffusing region intermediate a distal end and a proximal end of said optical fiber.

32. A method as defined in claim 21 further comprising directing light through said optical fiber and monitoring light output from said diffusing region during the step of treating a selected region of said fiber.

33. A method as defined in claim 32 further comprising controlling the step of treating a selected region of said fiber in response to the light output from said diffusing region.

34. A method as defined in claim 32 further comprising controlling the step of treating a selected region of said fiber in response to the light output from said diffusing region to provide substantially uniform light output along the length of said diffusing region.

35. A method as defined in claim 21 wherein the step of providing said optical fiber comprises providing a polymeric optical fiber.

36. A method as defined in claim 21 wherein the step of providing said optical fiber comprises providing a polymethylmethacrylate optical fiber.

37. A method as defined in claim 21 further comprising controlling the step of treating a selected region of said fiber to provide substantially uniform light output along the length of said diffusing region.

38. A method as defined in claim 22 further comprising the step of removing particles of said particle jet that stick to said optical fiber.

39. A method as defined in claim 22 wherein the step of directing said particle jet comprises generating said particle jet with a miniature sandblasting device.

40. A light delivery device, comprising:
an optical fiber device comprising a polymeric optical fiber including a proximal end for coupling to a source of light and a diffusing region positioned distally of said proximal end, said polymeric optical fiber comprising a core and a cladding around said core, said diffusing region comprising a length of said polymeric optical fiber in which said cladding is partially removed to expose said core and in which the exposed core and the remaining cladding have a roughened surface for outwardly diffusing light carried through said polymeric optical fiber; and
a carrier device suitable for positioning said diffusing region near a selected region in a human body.

41. A light delivery device as in claim 40 wherein said polymeric optical fiber device is positioned within an elongated, flexible tube having a distal end and a proximal end, said tube having a region which is at least partially transparent or translucent to the light from said optical fiber device.

42. A device as defined in claim 40 wherein said core comprises polymethylmethacrylate (PMMA) and said cladding comprises fluorine-doped PMMA.

43. A device as in claim 40 wherein said device is a catheter.

44. A device as in claim 40 wherein said device is suitable for insertion through a cannula.

45. A light delivery catheter comprising:
an elongated, flexible tube having a distal end and a proximal end, and an optical fiber device positioned within said flexible tube for carrying light through said flexible tube, said optical fiber device comprising a polymeric optical fiber including a proximal end for coupling to a source of light and a diffusing region positioned distally of said proximal end, said polymeric optical fiber comprising a core and a cladding around said core, said diffusing region comprising a length of said polymeric optical fiber in which said cladding is partially removed to expose said core and in which the exposed core and the remaining cladding have a roughened surface for outwardly diffusing light carried through said polymeric optical fiber.

46. A method for fabricating an optical fiber device, comprising the steps of:
a) providing an elongated optical fiber including a core and a cladding around the core, said optical fiber having a longitudinal axis;
b) directing a particle jet at the optical fiber for partially removing said cladding and exposing said core and for roughening the exposed core and the remaining cladding;
c) rotating said optical fiber about said longitudinal axis with respect to said particle jet during step b); and
d) translating said optical fiber along said longitudinal axis with respect to said particle jet during step b) so as to form a diffusing region of said optical fiber in which said region has a roughened surface.

* * * * *